United States Patent [19]

Gangemi et al.

[11] Patent Number: 5,137,720
[45] Date of Patent: Aug. 11, 1992

[54] ANTIVIRAL COMBINATION, AND METHOD OF TREATMENT

[75] Inventors: J. David Gangemi, Columbia, S.C.; Heinz-Kurt Hochkeppel, Aesch, Switzerland

[73] Assignee: Ciba-Geigy Corporation, Ardsley, N.Y.

[21] Appl. No.: 750,711

[22] Filed: Aug. 20, 1991

Related U.S. Application Data

[63] Continuation of Ser. No. 310,255, Feb. 13, 1989, abandoned.

[30] Foreign Application Priority Data

Feb. 13, 1988 [GB] United Kingdom ............... 8803365

[51] Int. Cl.$^5$ ................................. A61K 37/66
[52] U.S. Cl. ..................... 424/85.7; 530/351; 530/331; 424/450; 424/92; 514/8
[58] Field of Search .............. 514/8; 424/450, 85.7, 424/92; 530/351, 331

[56] References Cited

U.S. PATENT DOCUMENTS 4,774,085 9/1988 Fidler ........................... 424/85.5

FOREIGN PATENT DOCUMENTS

76528/87 2/1988 Australia .
205404 12/1986 European Pat. Off. .

OTHER PUBLICATIONS

Goeddel et al., *Nature* 290: 20–26 (1981).
Utsugi et al., Journal of Immunology vol. 136 No. 3 (1986) pp. 1117–1122.
Saiki et al., Journal of Immunology, vol. 135, No. 1, pp. 684–688 (1985).
Fidler et al., Journal of Immunology, vol. 135, No. 6, pp. 4289–4296 (1985).
Sone et al., Int. J. Cancer, vol. 38, pp. 495–500 (1986).

*Primary Examiner*—David L. Lacey
*Assistant Examiner*—Shelly J. Guest
*Attorney, Agent, or Firm*—Irving M. Fishman; Karen G. Kaiser

[57] ABSTRACT

Described is a synergistic pharmaceutical combination preparation comprising as component A a hybrid α-interferon the structure of which is derived from human interferon-α-D and -α-B gene fragments and as component B a muramylpeptide. The preparation can be used for treating viral diseases or reducing the formation of metastases of certain tumors.

12 Claims, No Drawings

ANTIVIRAL COMBINATION, AND METHOD OF TREATMENT

This application is a continuation of application Ser. No. 310,255, filed Feb. 13, 1989, now abandoned.

The invention relates to a pharmaceutical combination preparation (composition) comprising an interferon selected from certain types of α-interferons and a muramylpeptide, to said combination for use in a method of treatment of the human or animal body, especially suffering from diseases caused by certain types of viruses or tumor, as well as to a corresponding method of treating warm-blooded animals including humans.

The invention relates especially to a pharmaceutical combination preparation comprising as component A a hybrid α-interferon, the structure of which is derived from human interferon-α-D and -α-B gene fragments and as component B a muramylpeptide or a pharmaceutically acceptable salt of a muramylpeptide having at least one salt-forming group together with a pharmaceutically acceptable carrier.

An α-interferon derived from human interferon-α-D and -α-B gene fragments to be used as component A is a recombinant human α-interferon B/D hybrid, especially a hybrid α-interferon as described in European patent application 205 404 which is equivalent to U.S. Pat. No. 4,885,166, e.g. the interferons designated "B$_1$B$_2$B$_3$D$_4$", "B$_1$B$_2$D$_3$B$_4$", "B$_1$D$_2$B$_3$D$_4$", "B$_1$D$_2$D$_3$B$_4$", "B$_1$D$_2$D$_3$D$_4$" or, preferably, the interferon designated "B$_1$D$_2$B$_3$B$_4$".

A said α-interferon is also the leukocyte interferon hybrid designated "BD" which is disclosed in column 3 in connection with FIG. 3 of U.S. Pat. No. 4,414,150. Said U.S. patent is expressly referred to and discussed in the above-mentioned European patent application 205 404. Said interferon hybrid "BD" is nearly identical to the hybrid "B$_1$B$_2$D$_3$D$_4$".

The hybrid α-interferons used as component A have preferably about 166 amino acids and consist of, preferably four, fragments of human lymphoblastoid or leukocyte interferons-α-B and -α-D. Fragment B$_1$ consists of amino acids 1–60 of interferon-α-B, fragment B$_2$ consists of amino acids 61–92 of interferon-α-B, and fragments B$_3$ and B$_4$ consist of amino acids 93–150 and 151–166 of interferon-α-B, respectively. Similarly fragments D$_1$, D$_2$, D$_3$ and D$_4$ consist of amino acids 1–60, 61–92, 93–150 and 151–166 of interferon-α-D, respectively. Hybrid interferons starting with fragment B$_1$ are preferred. Therefore, component A is especially a hybrid α-interferon having a total of 166 amino acids and being composed of four subsequences corresponding in respect to amino acid identity and number to amino acid sequences of human lymphoblastoid or leukocyte interferon-α-β or -α-D, i.e. amino acids 1–60 of interferon-α-B, amino acids 61–92 of interferon-α-B or -α-D, amino acids 93–150 of interferon-α-B or -α-D and amino acids 151–166 of interferon-α-B or -α-D, each hybrid having at least one of said subsequences of interferon-α-B and interferon-α-D.

The hybrid α-interferon polypeptide "B$_1$B$_2$B$_3$D$_4$" has the formula

| Cys | Asp | Leu | Pro | Gln | Thr | His | Ser | Leu | Gly | Asn | Arg | Arg | Ala | Leu | Ile | Leu |
|---|---|---|---|---|---|---|---|---|---|---|---|---|---|---|---|---|
| Leu | Ala | Gln | Met | Arg | Arg | Ile | Ser | Pro | Phe | Ser | Cys | Leu | Lys | Asp | Arg | His |
| Asp | Phe | Glu | Phe | Pro | Gln | Glu | Glu | Phe | Asp | Asp | Lys | Gln | Phe | Gln | Lys | Ala |
| Gln | Ala | Ile | Ser | Val | Leu | His | Glu | Met | Ile | Gln | Gln | Thr | Phe | Asn | Leu | Phe |
| Ser | Thr | Lys | Asp | Ser | Ser | Ala | Ala | Leu | Asp | Glu | Thr | Leu | Leu | Asp | Glu | Phe |
| Tyr | Ile | Glu | Leu | Asp | Gln | Gln | Leu | Asn | Asp | Leu | Glu | Ser | Cys | Val | Met | Gln |
| Glu | Val | Gly | Val | Ile | Glu | Ser | Pro | Leu | Met | Tyr | Glu | Asp | Ser | Ile | Leu | Ala |
| Val | Arg | Lys | Tyr | Phe | Gln | Arg | Ile | Thr | Leu | Tyr | Leu | Thr | Glu | Lys | Lys | Tyr |
| Ser | Ser | Cys | Ala | Trp | Glu | Val | Val | Arg | Ala | Glu | Ile | Met | Arg | Ser | Leu | Ser |
| Leu | Ser | Thr | Asn | Leu | Gln | Glu | Arg | Leu | Arg | Arg | Lys | Glu | | | | |

The hybrid α-interferon polypeptide "B$_1$B$_2$D$_3$B$_4$" has the formula

| Cys | Asp | Leu | Pro | Gln | Thr | His | Ser | Leu | Gly | Asn | Arg | Arg | Ala | Leu | Ile | Leu |
|---|---|---|---|---|---|---|---|---|---|---|---|---|---|---|---|---|
| Leu | Ala | Gln | Met | Arg | Arg | Ile | Ser | Pro | Phe | Ser | Cys | Leu | Lys | Asp | Arg | His |
| Asp | Phe | Glu | Phe | Pro | Gln | Glu | Glu | Phe | Asp | Asp | Lys | Gln | Phe | Gln | Lys | Ala |
| Gln | Ala | Ile | Ser | Val | Leu | His | Glu | Met | Ile | Gln | Gln | Thr | Phe | Asn | Leu | Phe |
| Ser | Thr | Lys | Asp | Ser | Ser | Ala | Ala | Leu | Asp | Glu | Thr | Leu | Leu | Asp | Glu | Phe |
| Tyr | Ile | Glu | Leu | Asp | Gln | Gln | Leu | Asn | Asp | Leu | Glu | Ala | Cys | Val | Met | Gln |
| Glu | Glu | Arg | Val | Gly | Glu | Thr | Pro | Leu | Met | Asn | Ala | Asp | Ser | Ile | Leu | Ala |
| Val | Lys | Lys | Tyr | Phe | Arg | Arg | Ile | Thr | Leu | Tyr | Leu | Thr | Glu | Lys | Lys | Tyr |
| Ser | Pro | Cys | Ala | Trp | Glu | Val | Val | Arg | Ala | Glu | Ile | Met | Arg | Ser | Phe | Ser |
| Leu | Ser | Ile | Asn | Leu | Gln | Lys | Arg | Leu | Lys | Ser | Lys | Glu | | | | |

The hybrid α-interferon "B$_1$D$_2$B$_3$D$_4$" has the formula

| Cys | Asp | Leu | Pro | Gln | Thr | His | Ser | Leu | Gly | Asn | Arg | Arg | Ala | Leu | Ile | Leu |
|---|---|---|---|---|---|---|---|---|---|---|---|---|---|---|---|---|
| Leu | Ala | Gln | Met | Arg | Arg | Ile | Ser | Pro | Phe | Ser | Cys | Leu | Lys | Asp | Arg | His |
| Asp | Phe | Glu | Phe | Pro | Gln | Glu | Glu | Phe | Asp | Asp | Lys | Gln | Phe | Gln | Lys | Ala |
| Gln | Ala | Ile | Ser | Val | Leu | His | Glu | Met | Ile | Gln | Gln | Ile | Phe | Asn | Leu | Phe |
| Thr | Thr | Lys | Asp | Ser | Ser | Ala | Ala | Trp | Asp | Glu | Asp | Leu | Leu | Asp | Lys | Phe |
| Cys | Thr | Glu | Leu | Tyr | Gln | Gln | Leu | Asn | Asp | Leu | Glu | Ser | Cys | Val | Met | Gln |
| Glu | Val | Gly | Val | Ile | Glu | Ser | Pro | Leu | Met | Tyr | Glu | Asp | Ser | Ile | Leu | Ala |
| Val | Arg | Lys | Tyr | Phe | Gln | Arg | Ile | Thr | Leu | Tyr | Leu | Thr | Glu | Lys | Lys | Tyr |
| Ser | Ser | Cys | Ala | Trp | Glu | Val | Val | Arg | Ala | Glu | Ile | Met | Arg | Ser | Leu | Ser |
| Leu | Ser | Thr | Asn | Leu | Gln | Glu | Arg | Leu | Arg | Arg | Lys | Glu | | | | |

The hybrid α-interferon "B$_1$D$_2$D$_3$B$_4$" has the formula

| Cys | Asp | Leu | Pro | Gln | Thr | His | Ser | Leu | Gly | Asn | Arg | Arg | Ala | Leu | Ile | Leu |
|---|---|---|---|---|---|---|---|---|---|---|---|---|---|---|---|---|

-continued

| Leu | Ala | Gln | Met | Arg | Arg | Ile | Ser | Pro | Phe | Ser | Cys | Leu | Lys | Asp | Arg | His |
| Asp | Phe | Glu | Phe | Pro | Gln | Glu | Glu | Phe | Asp | Asp | Lys | Gln | Phe | Gln | Lys | Ala |
| Gln | Ala | Ile | Ser | Val | Leu | His | Glu | Met | Ile | Gln | Gln | Ile | Phe | Asn | Leu | Phe |
| Thr | Thr | Lys | Asp | Ser | Ser | Ala | Ala | Trp | Asp | Glu | Asp | Leu | Leu | Asp | Lys | Phe |
| Cys | Thr | Glu | Leu | Tyr | Gln | Gln | Leu | Asn | Asp | Leu | Glu | Ala | Cys | Val | Met | Gln |
| Glu | Glu | Arg | Val | Gly | Glu | Thr | Pro | Leu | Met | Asn | Ala | Asp | Ser | Ile | Leu | Ala |
| Val | Lys | Lys | Tyr | Phe | Arg | Arg | Ile | Thr | Leu | Tyr | Leu | Thr | Glu | Lys | Lys | Tyr |
| Ser | Pro | Cys | Ala | Trp | Glu | Val | Val | Arg | Ala | Glu | Ile | Met | Arg | Ser | Phe | Ser |
| Leu | Ser | Ile | Asn | Leu | Gln | Lys | Arg | Leu | Lys | Ser | Lys | Glu | | | | |

The hybrid α-interferon polypeptide "B₁D₂D₃D₄" has the formula

| Cys | Asp | Leu | Pro | Gln | Thr | His | Ser | Leu | Gly | Asn | Arg | Arg | Ala | Leu | Ile | Leu |
| Leu | Ala | Gln | Met | Arg | Arg | Ile | Ser | Pro | Phe | Ser | Cys | Leu | Lys | Asp | Arg | His |
| Asp | Phe | Glu | Phe | Pro | Gln | Glu | Glu | Phe | Asp | Asp | Lys | Gln | Phe | Gln | Lys | Ala |
| Gln | Ala | Ile | Ser | Val | Leu | His | Glu | Met | Ile | Gln | Gln | Ile | Phe | Asn | Leu | Phe |
| Thr | Thr | Lys | Asp | Ser | Ser | Ala | Ala | Trp | Asp | Glu | Asp | Leu | Leu | Asp | Lys | Phe |
| Cys | Thr | Glu | Leu | Tyr | Gln | Gln | Leu | Asn | Asp | Leu | Glu | Ala | Cys | Val | Met | Gln |
| Glu | Glu | Arg | Val | Gly | Glu | Thr | Pro | Leu | Met | Asn | Ala | Asp | Ser | Ile | Leu | Ala |
| Val | Lys | Lys | Tyr | Phe | Arg | Arg | Ile | Thr | Leu | Tyr | Leu | Thr | Glu | Lys | Lys | Tyr |
| Ser | Pro | Cys | Ala | Trp | Glu | Val | Val | Arg | Ala | Glu | Ile | Met | Arg | Ser | Leu | Ser |
| Leu | Ser | Thr | Asn | Leu | Gln | Glu | Arg | Leu | Arg | Arg | Lys | Glu | | | | |

The hybrid α-interferon "B₁D₂B₃B₄" has the formula

| Cys | Asp | Leu | Pro | Gln | Thr | His | Ser | Leu | Gly | Asn | Arg | Arg | Ala | Leu | Ile | Leu |
| Leu | Ala | Gln | Met | Arg | Arg | Ile | Ser | Pro | Phe | Ser | Cys | Leu | Lys | Asp | Arg | His |
| Asp | Phe | Glu | Phe | Pro | Gln | Glu | Glu | Phe | Asp | Asp | Lys | Gln | Phe | Gln | Lys | Ala |
| Gln | Ala | Ile | Ser | Val | Leu | His | Glu | Met | Ile | Gln | Gln | Ile | Phe | Asn | Leu | Phe |
| Thr | Thr | Lys | Asp | Ser | Ser | Ala | Ala | Trp | Asp | Glu | Asp | Leu | Leu | Asp | Lys | Phe |
| Cys | Thr | Glu | Leu | Tyr | Gln | Gln | Leu | Asn | Asp | Leu | Glu | Ser | Cys | Val | Met | Gln |
| Glu | Val | Gly | Val | Ile | Glu | Ser | Pro | Leu | Met | Tyr | Glu | Asp | Ser | Ile | Leu | Ala |
| Val | Arg | Lys | Tyr | Phe | Gln | Arg | Ile | Thr | Leu | Tyr | Leu | Thr | Glu | Lys | Lys | Tyr |
| Ser | Ser | Cys | Ala | Trp | Glu | Val | Val | Arg | Ala | Glu | Ile | Met | Arg | Ser | Phe | Ser |
| Leu | Ser | Ile | Asn | Leu | Gln | Lys | Arg | Leu | Lys | Ser | Lys | Glu | | | | |

The muramylpeptide is e.g. a muramyldipeptide or a muramyltripeptide as described in British patents 1 570 625 and 1 571 133 the latter being equivalent to U.S. Pat. Nos. 4,082,735 and 4,082,736 as well as in French patent application having the publication no. 2 343 482, or preferably a muramylpeptide substituted by a phosphatidyl moiety, e.g. as described in European patents 25 495 which is equivalent to U.S. Pat. No. 4,406,890 and 102 319. Preferred muramyldipeptides are N-acetyl-muramyl-L-alanyl-D-isoglutamine, N-acetyl-muramyl-L-threonyl-D-isoglutamine and N-acetyl-demethyl-muramyl-L-alanyl-D-isoglutamine. A preferred phosphatidyl-muramylpeptide is N-acetyl-muramyl-L-alanyl-D-isoglutaminyl-L-alanine-2-(1,2-dipalmitoyl-sn-glycero-3-hydroxyphosphoryloxy)-ethylamide (abbreviated: MTP-PE) having the formula:

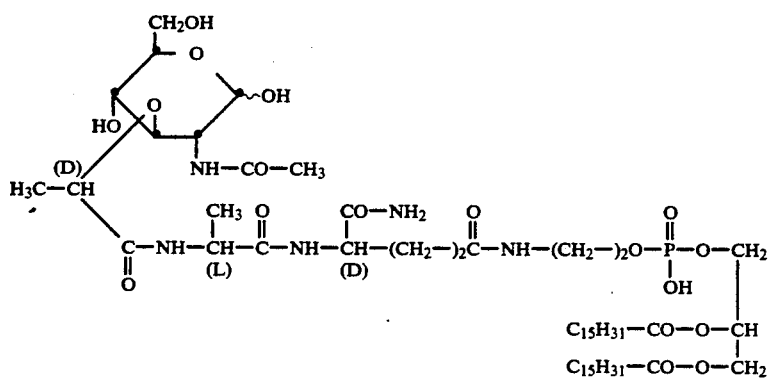

Salt-forming groups in a muramylpeptide are especially acidic groups, e.g. carboxy groups or phosphoric acid groups, or basic groups, e.g. amino groups. Pharmaceutically acceptable salts of muramylpeptides having an acidic group are e.g. alkali metal salts, e.g. potassium or, preferably, sodium salts, or alkaline earth metal salts, e.g. calcium salts, or salts with ammonia or a suitable organic amine, e.g. triethylamine. Salts of muramylpeptides having a basic group are acid addition salts with suitable inorganic or organic acids, e.g. trifluoroacetic acid.

The combination preparation may either contain the active ingredients A and B in a manner which necessitates administering them at the same time and by the same route or comprise the active ingredients separately (kit of parts) allowing for administration at different times and/or by different routes.

According to the present invention it has surprisingly been found that the components A and B act together in a manner so that one component enhances the activity of the other (synergistic effect).

A combination preparation according to the present invention may be used e.g. for reducing or inhibiting the formation of metastases in warm-blooded animals in the case of some tumours, especially of the lung, as can be demonstrated experimentally e.g. in the $B_{16}$-$BL_6$-melanoma model and in the Lewis lung carcinoma, administration in liposomes being especially advantageous. A said combination preparation may be also used for the prophylaxis and especially treatment of diseases caused by viruses in warm-blooded animals including humans, especially by viruses specified in detail hereinafter [for nomenclature cf. J. L. Melnick, Prog. med. Virol. 26, 214–232 (1980) and 28, 208–221 (1982)]: Picornaviridae, myxoviruses and most especially Herpesviridae. Myxoviruses are preferably influenza viruses, types A and B, and parainfluenza viruses. Herpesviridae are preferably Alphaherpesvirinae, as particularly simplex viruses, e.g. human herpes simplex viruses of types 1 and 2, but also Betaherpesvirinae, such as, especially, human cytomegaloviruses.

The daily dose of one of the above-mentioned $\alpha$-interferons to be applied to a warm-blooded animal in combination with a muramylpeptide is about $10^4$ to about $10^7$ units per kg body weight, especially about $10^5$ to about $10^6$ units/kg, e.g. $5 \times 10^6$ units/kg, or about 10 $\mu$g/kg. The quantity of the interferons may be expressed not only in terms of weight but also in terms of their biological, e.g. antiviral, activity and expressed in "units". The antiviral titres are determined as the reduction of cytopathic effect according to the method of S. Rubinstein et al. [J. virol. 37, 755 (1981)] using vesicular stomatitis virus (VSV) as the challenge virus on bovine (MDBK) and human (WISH) cells [cf. A. Meister et al., J. gen. Virol. 67 (1986), 1633 to 1643, especially page 1634].

The daily dose of one of the above-mentioned muramylpeptides to be applied to a warm-blooded animal in combination with one of said $\alpha$-interferons is about 0.005 mg/kg to about 5 mg/kg, especially about 0.01 mg/kg to about 1 mg/kg, preferably about 0.1 mg/kg.

The dose does not increase in a linear manner with the body weight. Thus the dose for a warm-blooded animal of approximately 70 kg body weight, for example a human, is about 0.2 mg to about 20 mg, preferably between 1 and 10 mg of said muramylpeptide and of said $\alpha$-interferon.

The ratio by weight of said muramylpeptide versus said interferon wherein the synergistic effect occurs is preferably about 0.4/1 to about 400/1, especially about 1/1 to about 100/1, e.g. 10/1 to 40/1.

Preferred is a pharmaceutical combination preparation for the treatment of an infection caused by viruses or for the activation of macrophages in a warm-blooded animal comprising an antivirally effective or macrophages activating amount of a combination of the hybrid $\alpha$-interferon polypeptide $B_1D_2B_3B_4$ as component A and a pharmaceutically acceptable salt of N-acetyl-muramyl-L-alanyl-D-isoglutaminyl-L-alanine-2-(1,2-dipalmitoyl-sn-glycero-3-hydroxyphosphoryloxy)-ethylamide as component B wherein the ratio by weight of B versus A is 1/1 to 100/1.

The invention relates also to a method of treating a warm-blooded animal including a human suffering from a disease caused by viruses or tumor comprising administering to said animal an antivirally effective amount, or an amount preventing the formation of metastases, of a hybrid $\alpha$-interferon, the structure of which is derived from human interferon-$\alpha$-D and -$\alpha$-B gene fragments, and a muramylpeptide in a weight ratio of B versus A of 0.4/1 to 400/1.

The active ingredients may be administered by a different route and at a different time or, preferably, the same route and the same time. The route of administration depends inter alia on the disease to be cured and is especially parenteral, e.g. intravenous, or is topical, including vaginal, rectal or intranasal. If required, the administration of the active ingredients can be repeated until there is an improvement in the disease. Often, however, one administration is inadequate.

The particular mode of administration and the dosage will be selected by the attending physician taking into account the particulars of the patient, the disease and the disease state involved.

Preferred is a method of activating macrophages or of treating an infection caused by Herpesviridae in a warm-blooded animal comprising administering to said animal a macrophages activating or antivirally effective amount of a combination of the hybrid $\alpha$-interferon polypeptide $B_1D_2B_3B_4$ as component A and a pharmaceutically acceptable salt of N-acetyl-muramyl-L-alanyl-D-isoglutaminyl-L-alanine-2-(1,2-dipalmitoyl-sn-glycero-3-hydroxyphosphoryloxy)-ethylamide as component B wherein the ratio by weight of B versus is 1/1 to 100/1.

The pharmaceutically acceptable carrier material present in the preparation according to the invention may comprise liposomes or other, more conventional, inorganic or organic, solid or liquid pharmaceutically acceptable carriers.

In some cases, e.g. whenever a transport of the active ingredients to the lung is desired, it is advantageous to encapsulate the muramylpeptide component or the interferon or both components in liposomes.

Liposomes have been described in the literature in numerous publications. Their structure and use has been made subject matter of intensive research work. Depending on their shell structure, a distinction is made between unilamellar liposomes or vesicles (ULV) and multilamellar liposomes or vesicles (MLV). In some publications, the term "vesicle" strictly applies to unilamellar liposomes. ULV have a spherical shell consisting of one double layer of lipids, especially phospholipids, and MLV a spherical shell consisting of several double layers arranged in an onion-shell like pattern. The spherical shell may consist of phospholipids such as phosphatidylcholine, phosphatidylethanolamine or phosphatidic acid and optionally "neutral" lipids such as cholesterol. This shell encapsulates an internal volume containing the aqueous phase and pharmacologically active compounds.

Depending upon the degree of lipophility and other parameters, such as temperature or concentration, the encapsulated compounds are present in the enclosed aqueous phase and/or in the double layer(s).

Pharmaceutical administration systems based on liposomes have been described in the general review issued by G. Gregoriadis, Liposome Technology, Vol. II, Incorporation of Drugs, Proteins and Genetic Material, CRC Press 1984. Such systems have the advantage that biologically active material can be introduced into tissues by phagocytosis, especially into tissues of the reticulo-endothelial system. For example, a transport mechanism is known for antibiotics being introduced into infected tissues by phagocytosis thus causing the improved removal or destruction of the infecting microorganism. Endocytosis also is a helpful mechanism in the combat of centres of inflammation. Antirheumatic pharmaceuticals encapsulated in liposomes are preferably introduced into infected tissues as compared to "healthy" tissues. Moreover, cytostatic agents, commonly known as "anticancer drugs", can be introduced into specific organs of the reticulo-endothelial system (liver, spleen or marrow). Additionally, due to filtration in the capillaries of the lung and subsequent transport by migrating monocytes, biologically active material, for example compounds having immunomodulatory properties, can be concentrated in alveolar macrophages. This results in an improved action on metastatic lung tumors and in a simultaneous reduction of toxicity.

For the purposes of the present invention liposomes consisting of a phosphatidyl-choline and a phosphatidylserine are preferably used, especially those consisting of synthetical (1-palmitoyl-2-oleoyl-3-sn-phosphatidyl)-choline and a pharmaceutically acceptable salt, e.g. a sodium salt, of a synthetical (1,2-dioleoyl-3-sn-phosphatidyl)-L-serine, especially in a 7:3 molar ratio.

The manufacture of the liposomes is described e.g. in European patent application 178 624. If the active component A or B to be encapsulated is lipophilic, a homogeneous mixture of the phospholipids and said active component is dispersed in an aqueous phase. If the active component A or B to be encapsulated is water-soluble a homogeneous mixture of the phospholipids is dispersed in an aqueous phase containing said active component A or B. If necessary, the aqueous dispersion is buffered to a pH-value between about 7.0 and 7.8 and concentrated. The liposomes may be also separated from the aqueous phase.

The homogeneous mixture of the phospholipids is prepared by formation of a film or a lyophilisate of the phospholipids. The film is prepared by dissolving the phospholipids in an organic solvent and stripping the solvent.

Suitable solvents are, for example, unsubstituted or substituted, for example halogenated, aliphatic or cycloaliphatic hydrocarbons, for example n-hexane, cyclohexane, methylenechloride, or chloroform, alcohols, for example methanol or ethanol, lower alkanecarboxylic acid esters or amides, for example acetic acid ethylester or dimethylformamide, or ethers, for example diethylether, tetrahydrofurane or dioxane, or mixtures of these solvents.

The organic solvent is subsequently stripped by applying a vacuum, preferably a high vacuum, or by blowing off with an inert gas, for example nitrogen. The lyophilisate is formed by lyophilizing in a conventional manner a solution of the phospholipids in an organic solvent according to the method as described in the U.S. Pat. No. 4,311,712. Suitable solvents are in the solid form together with the phospholipids at the temperature of the lyophilisation process and are having a melting point of more than 0° C., for example glacial acetic acid, benzene or dioxane, especially tert-butanol.

A homogeneous mixture may also be prepared by spray-drying a solution of the phospholipids in an organic solvent having a low boiling point such as chloroform. A powder is obtained by this method.

The ratio of the phosphatidyl serine component to the phosphatidyl choline component in the homogeneous mixture is approximately 10 v. 90 up to 50 v. 50 mole percent. Preferred is the ratio 30 v. 70 mole percent. The approximate ratio of the molar amounts of the encapsulated active material (muramyldipeptide in combination with α-interferon) divided by the total amount of the phospholipids is about 0.0001 to 0.1 v. 1.0, preferably 0.005 to 0.01 v. 1.0. This means that preferably about a hundred-fold molar excess of the phospholipids are used.

The dispersion is carried out by agitation of the aqueous phase (vigorous shaking—Vortex mixer or stirring at high speed). A mixture of small, large, unilamellar or multilamellar liposomes is formed spontaneously at a high rate without supplying external energy. Approximately 0.1 to 40 percent per weight, preferably 2 to 20 percent per weight, of the homogeneous mixture relative to the total weight of the aqueous dispersion can be dispersed in the aqueous phase. Preferably, such dispersions are further diluted to about 1 micromole lipid per ml. The liposome dispersions of that concentration have entrapped approximately 2.5 microliters of the aqueous phase per micromole of the lipid.

The preparation of the pharmaceutical compositions according to the present invention in the form of liposomes can also be carried out by other methods known in the art for preparing liposomes, for example by sonication with supersonic waves, by infusion methods or reversed phase evaporation.

The dispersion step is performed at temperatures below 60°, preferably at room temperature. In view of a potential thermal sensitivity of the encapsulated material, the dispersion is carried out under cooling and, optionally, under inert gas atmosphere, for example nitrogen or argon atmosphere.

The mixture of phospholipids (I) and (II) which can be used for the manufacture of the pharmaceutical compositions according to the invention has, after dispersion in aqueous phase, a phase transition temperature (liquid-gel form) of less than approximately 37° C. The liposome dispersion can be manufactured without heating.

The liposomes obtained can be made storage stable in the aqueous phase up to several weeks or months after addition of stabilizers, for example mannite or lactose.

The size of the liposomes formed depends, inter alia, on the structure of the active ingredient and the lipid component, the mixing ratio of the components and the concentration of these components in the aqueous dispersion. Thus, for example, by increasing or reducing the concentration of the lipid component it is possible to produce aqueous phases having a high content of small or large liposomes.

The separation of small liposomes from large liposomes is effected by means of conventional separation methods, for example sedimentation of the large liposomes in an ultracentrifuge, gel filtration or extrusion through straight-pored filters. For example, on centrifuging, for example from 5 to 30 minutes in a rotational field giving rise to an inertial force equivalent to a gravitational field of 5000–40,000× g, large liposomes are deposited, whilst small liposomes remain dispersed and can be decanted off. After repeated centrifugation, complete separation of the large liposomes from the small liposomes is achieved.

Liposomes in the aqueous phase having a diameter greater than $6.0 \times 10^{-8}$ m, for example large multilamellar liposomes, can be separated off by gel filtration, for example with Sepharose or Sephacryl as carriers.

By extrusion through straight-pored filters, for example membrane filters of the Nucleopore ® or polycarbonate type having a pore diameter of approximately $1.0 \times 10^{-7}$–$1.0 \times 10^{-9}$ m at a pressure of approximately from 0.1 to 1.5 bar and a filtration rate of approximately 20 ml/h, it is possible to obtain a particularly uniform size distribution of the liposomes.

The formation of liposomes and their content in the aqueous phase can be detected in a manner known per se by using various physical analytical methods, for example by microscopy of freeze-fracture samples and thin sections in an electron microscope, by X-ray defraction, by dynamic light scattering, by mass determination of the filtrate in an analytical ultracentrifuge and, especially, by spectroscopy, for example in the nuclear magnetic resonance spectrum ($^1H$, $^{13}C$ and $^{31}P$).

The phospholipids used for the preparation of the liposomes are known. Some of them are commercially available (Avanti, Fluka, Serva). The preparation of (1,2-di-oleoyl-3-sn-phosphatidyl)-(L)-serine and of analogous lipids is described by Browning J. and Seelig J. in Chem. and Phys. of Lipids 24 (1979) 103-118.

The buffer solutions of pH 7,0 to 7,8 preferably are sterile phosphate buffer solutions based on the dihydrogenphosphate/hydrogenphosphate equilibrium ($KH_2PO_4/Na_2HPO_4$). The preparation of these buffer solutions is described in standard manuals, for example "Hager's Handbuch der Pharmazeutischen Praxis", Springer Verlag, Vol. 1, pg. 357-359. Especially sterile, isotonic calcium-free buffer solution of pH 7.2 (Dulbecco) or Hank's Balanced Salt Solution (M. A. Bioproducts, Walkersville, Md. U.S.A.) is used.

For parenteral administration, the liposomes are dispersed in a sterile aqueous solution which serves as a carrier liquid, for example sterile, calcium-free, isotonic saline or glucose solution, buffered to pH 7.0-7.8, preferably 7.2-7.4.

For topical administration, the liposome-containing aqueous dispersion, buffered to pH 7.0-7.8, preferably 7.2-7.4, is mixed with customary solid carriers, for example thickeners, for example hydroxypropylcellulose, and suitable preservatives, antioxidants or perfumes and used in the form of a lotion or gel for application to the skin or the mucous membranes.

The more conventional parenteral formulations are especially injectable fluids that are effective in various manners, such as intravenously, intramuscularly, intraperitoneally, intranasally, intradermally or subcutaneously. Such fluids are preferably isotonic aqueous solutions or suspensions which can be prepared before use, for example from lyophilised preparations which contain the active ingredient alone or together with a pharmaceutically acceptable carrier. The pharmaceutical preparations may be sterilized and/or contain adjuncts, for example preservatives, stabilisers, wetting agents and/or emulsifiers, solubilisers, salts for regulating the osmotic pressure and/or buffers. The present pharmaceutical preparations, which may, if desired, contain further pharmacologically valuable substances, are produced in a manner known per se, for example by means of conventional dissolving of lyophilising processes, and contain from approximately 0.1% to 20%, especially from approximately 1% to approximately 10%, and in the case of lyophilisates up to 100%, of the active ingredient.

The more conventional topical formulations are e.g. suppositories, creams, ointments, pastes, gels, lipsticks, drops, sprays, foams or tinctures containing the conventional carrier materials known to a person skilled in the art and described e.g. in European patent 102 319.

The following Examples illustrate the invention. Temperatures are given in degrees Celsius.

ABBREVIATIONS

CEF: Chicken embryonic fibroblasts
HBSS: Hank's balanced salt solution
HSV-1: Herpes simplex virus, type 1
MEM: Eagle's minimum essential medium
MTP-PE: N-acetyl-muramyl-L-alanyl-D-isoglutaminyl-L-alanine-2-(1,2-di-palmitoyl-sn-glycero-3-hydroxyphosphoryloxy)-ethylamide-sodium salt
OOPS: synthetical (1,2-di-oleoyl-3-sn-phosphatidyl)-L-serine-sodium salt
PBS: Phosphate buffered saline
POPC: synthetical (1-palmitoyl-2-oleoyl-3-sn-phosphatidyl)-choline
RPMI: Rosewell Park Memorial Institute, Buffalo, N.Y. U.S.A.

EXAMPLE 1

Cytotoxicity

A. Materials and Methods

Animals

Specific pathogen free white rats (Tif: RAI f) weighing between 150 and 200 grams were used. These animals were routinely screened for the presence of adventitious agents prior to use.

Cell Cultures

Macrophage-mediated cytotoxicity was assessed against syngeneic MADB-200 adenocarcinoma target cells available from the American Type Culture Collection, ATCC. These cells were maintained as monolayer cultures in MEM supplemented with 10% fetal calf serum. Cultures were maintained at 37° C. in a humidified atmosphere containing 5% $CO_2$. Cultures were routinely tested for the presence of mycoplasma.

Collection and Cultivation of Rat Alveolar Macrophages

Alveolar macrophages (AM) were collected by transtracheal lavage (Brownbill and Schumann, Cancer Immunol. Immunother. 20, 11–17, 1985). The cells recovered from lavage fluids were centrifuged at 400× g for 10 minutes, suspended in serum-free medium, and plated into 96-well Microtest II plastic tissue culture dishes at $5 \times 10^4$ cells per well. After incubation for 60 minutes, cells were washed with HBSS to remove non-adherent cells were macrophages as determined by cytochemical criteria.

In vitro Activation of Rat Alveolar Macrophages

Purified cultures of rat alveolar macrophages were incubated at 37° C. for 1 hour with 0.2 ml of control medium, recombinant alpha $B_1D_2B_3B_4$, MTP-PE, or a combination of alpha $B_1D_2B_3B_4$ and MTP-PE. To these treated cells, $5 \times 10^3$ MADB-200 tumor cells were added and allowed to incubate for 72 hours at 37° C. Thus, 50,000 macrophages were incubated with 5000 tumor cells.

In vitro Assay of Alveolar Macrophage-mediated Cytoxicity

A colorimetric assay using crystal violet staining of remaining MADB-200 tumor cells was used to determine macrophage cytotoxicity (Brownbill and Schumann, Cancer Immunol. Immunother. 20, 11–17, 1985). Briefly, following incubation, wells are washed with HBSS and the remaining cells fixed with formalin and stained with crystal violet. Each well is thoroughly washed after staining, the cells decolorized with alcohol, and the extract read with a colorimeter. The % cytotoxic activity of alveolar macrophages was calculated as follows:

$$1 - \frac{\text{Adsorbance of (treated alveolar macrophages + tumor cells)} - \text{adsorbance of alveolar macrophages alone}}{\text{Adsorbance of control alveolar macrophages + tumor cells}} \times 100$$

B. Results

Combined effects of MTP-PE and recombinant alpha $B_1D_2B_3B_4$ interferon on rat alveolar macrophage activation.

| MTP-PE [μg/ml] | % Cytotoxicity Alpha Interferon $B_1D_2B_3B_4$ | | | | |
|---|---|---|---|---|---|
| | 0 | 1500 | 5000 | 15000 | [units/ml] |
| | 0 | 0.01 | 0.033 | 0.1 | [μg/ml] |
| 0.0 | 0 | 1 | 14 | 34 | |
| 0.01 | 0 | 26 | 23 | 39 | |
| 0.03 | 7 | 16 | 30 | 54 | |
| 0.1 | 10 | 35 | 41 | 81 | |

EXAMPLE 2

Herpes pneumonitis

A. Materials and Methods

Animals

Three to four week-old female C3H/OLA mice were obtained from Harlan Breeding Laboratories (England). Mice were screened for the presence of sendai virus and other adventitious agents prior to being shipped. All mice were held for several days after arrival prior to being used.

Reagents

RPMI 1640 medium (a tissue culture medium containing all necessary growth factors), MEM, HBSS, and fetal calf serum were obtained from Grand Island Biological (GIBCO, New York, N.Y.). Recombinant alpha $B_1D_2B_3B_4$ interferon contains 0.1 mg = $1.5 \times 10^7$ units/ml. Liposome-encapsulated MTP-PE (lyophilized) contains 1 mg in 250 mg synthetic phospholipids consisting of POPC/OOPS in a 7:3 molar ratio. Recombinant rat gamma interferon was obtained from the primate center TNO (Holland) in a lyophilized form. Human alpha $B_1D_2B_3B_4$ interferon is able to bind to interferon receptors on many different animal species and induce a biological response. All reagents were free of endotoxin as determined by the Limulus amebocyte lysate assay (sensitivity limit of 0.125 ng/ml).

Virus and Cell Cultures

The VR3 strain of herpes simplex type 1 (HSV-1) virus was passaged in vero cells to obtain a working stock of virus. The virus used in these studies had a titer of $7.5 \times 10^7$ plaque forming units when assayed on vero cells and an $LD_{50}$ of 1000 when administered intranasally (0.05 ml) to three week old C3H/OLA mice. A two day plaque assay employing 0.5% agarose in the initial medium (MEM containing 10% fetal calf serum) overlay was used. Viable cells were stained with neutral red and the plaques counted. In some instances, lungs from infected mice were aseptically removed, washed free of contaminating blood, and homogenized with a Dounce Homogenizer. A 10% homogenate was prepared in RPMI and centrifuged for 15 minutes at 1000× g to remove cellular debris. These samples were stored at −80° C. until assayed for the presence of infectious virus using the plaque assay described above.

Herpes Pneumonitis Model

The pathobiology of intranasal infection with the VR3 strain of HSV-1 virus has been described by Nachtigal et al. (Am. J. Pathol. 115 [1984] and Gangemi et al. (J. Infect. Dis. 155 [1987], 510–517). Intranasal inoculation of four-week-old mice was followed by death within 10–12 days following infection. Microscopic examination of dead animals or of animals killed during the later phase of disease revealed extensive interstitial pneumonitis. Pulmonary lesions were characterized by a cellular inflammatory exudate with neutrophils, monocytes, and lymphocytes. In addition to pneumonitis, adrenal necrosis was a constant finding in infected mice. Adrenal necrotic foci enlarged with time after infection but showed very little inflammatory response. Immunostaining with polyclonal antibody to herpesvirus revealed deposits of viral antigen scattered throughout the lung and adrenal glands. Both organs appeared to be primary sites of virus replication when the intranasal route of infection was used. Pulmonary titers of HSV-1 increased to a maximum of $10^6$ plaque forming units per gram of wet tissue 48 hours after infection.

Preparation of Liposome-encapsulated MTP-PE and Alpha $B_1D_2B_3B_4$ Interferon 586 mg of sterile tert.-butanol, 1 mg of N-acetylmuramyl-L-alanyl-D-isoglutaminyl-L-alanine-2-(1,2-dipalmitoyl-sn-glycero-3-hydroxyphosphoryloxy)-ethylamide-sodium salt, 75 mg of (95% pure) sodium (1,2-dioleoyl-3-sn-phosphatidyl)-(L)-serine [manufactured according to Browning J. and Seelig J., Chem. and Physics of Lipids 24 (1979) 103–118] and 175 mg of (95% pure) (1-palmitoyl-2-oleoyl-3-sn-phosphatidyl)-choline (Avanti, Polar Lipids) are dissolved in a round-bottomed flask. The solution is sterile-filtered over Acrodisc ® ($2.0 \times 10^{-7}$ m), introduced into a sterile phial and frozen at −45°. The phial is dried in vacuo until a temperature of 25° is reached, and sealed under an argon atmosphere.

Alpha interferon is diluted in calcium and magnesium free PBS, and 2.5 ml is used to reconstitute 250 mg lyophilized synthetic lipids (POPC/OOPS, 7:3 molar ratio) containing 1 mg MTP-PE. This mixture is vigorously shaken in a Vortex mixer for 2 minutes and allowed to stand for 30 minutes prior to revortexing and the addition of another 2.5 ml of PBS. It is found (using $I^{125}$ labelled alpha interferon) that approximately 20% of the interferon is bound to liposomes following this reconstitution procedure. Liposomes prepared in this manner have the same physical properties as liposomes containing only MTP-PE and appear to follow the same body distribution profile following i.v. administration in rodents. Approximately 2-3 times more MTP-PE and interferon reach the lung when both substances are incorporated into liposomes as compared to unencapsulated forms. The association of alpha interferon to MTP-PE liposomes appears to be stable over an 8 hour period when stored at 40° C.

Procedure

Mice are inoculated intravenously with 0.2 ml of either placebo liposomes suspended in PBS, free-interferon $B_1D_2B_3B_4$ in PBS, liposome-encapsulated MTP-PE or a combination of liposome encapsulated MTP-PE and interferon $B_1D_2B_3B_4$. They are challenged intranasally with 0.05 ml of virus stock, diluted 1:10 in HBSS containing 0.2% bovine serum albumin, 2-3 hours following drug treatment.

Lungs are removed from infected mice 48 hours after infection and a 10% homogenate prepared. This homogenate is then plaque assayed on monolayers of vero cells. The virus titers expressed are based on the number of plaques in duplicate wells of 6-well (32 mm) plastic tissue culture plates. Lung weights are measured prior to homogenization as a 10% suspension. Three lungs per treatment group are analyzed. The standard deviation values represent the variability in duplicate samples from three lungs.

The dosage of alpha interferon used in these experiments is equivalent to one microgram of protein; thus, the MTP-PE:interferon ratio by weight is 40:1.

B. Results

As illustrated in the following table, virus replication in the lungs of mice receiving liposome-encapsulated MTP-PE and alpha interferon is significantly lower than when either agent is used alone.

Virus Titers in the Lungs of Mice Receiving Liposome-encapsulated Alpha $B_1D_2B_3B_4$ Interferon and MTP-PE

| Treatment | Plaque forming units per gram weight of lung 48 hours post infection +/− standard deviation |
|---|---|
| Placebo | 13,467 +/− 3995 |
| Apha $B_1D_2B_3B_4$ ($10^5$ units/mouse) | 8750 +/− 3594 |
| MTP-PE (40 μg/mouse) | 4100 +/− 1952 |
| MTP-PE (40 μg/mouse) + Alpha $B_1D_2B_3B_4$ ($10^5$ units/mouse) | 906 +/− 114 |

EXAMPLE 3

A. Materials and Methods

Animals

Female albino guinea pigs of the Pirbright strain, weighing 200–300 grams, were used to establish an animal viral model of herpes genitalis.

Virus and Cell Cultures

Herpes simplex virus type 2/MS obtained from ATCC (VR 540) is propagated and maintained in monolayers of human embryonic lung fibroblasts (HEL; FLOW 2002). The infected cells are incubated at 35° C. until 85–90% are destroyed (48–72 hours).

The virus is harvested by freezing and thawing of the medium and cells; this suspension is centrifuged at 1000 r.p.m. for 10 minutes and 0.5 ml of the supernatant is transferred to Cryotubes (NUNC) and stored at −180° C.

Herpes Genitalis in the Guinea Pig

Infection

Female albino guinea-pigs of the Pirbright strain, weighing 200–300 g, are infected intravaginally after gentle opening of the introitus vaginae with a forceps. Thereafter, pieces of fibrin foam (SEVAC, Prague) measuring 5×5×4 mm are impregnated with 0.05 ml containing about $10^4$ PFU of HSV 2/MS from cultures in HEL. These pieces are introduced intravaginally (1-2). The animals are kept in groups of 4–5 in type 4 Macrolon cages.

Treatment

Three days after infection, by which time the local symptomatology scores (see below) range from 3 to 6 in about 90% of the animals, these animals are divided at random into groups of 10–15 per preparation and untreated control. Treatment is started 72 hours after infection and administered twice daily for 5 days. One tenth of a milliliter is applied intravaginally and 0.1 ml extravaginally.

Evaluation of Symptoms

From the 3rd day onwards, the local symptoms are evaluated thrice weekly. The criteria applied in assessing the therapeutic effects of treatment are the rate and the degree of regression of overt signs of infection in the individual animals. The degree and severity of local symptoms are scored according to the following points system:

| | | |
|---|---|---|
| A. | Hyperaemia | |
| | slight, confined to parts of the vulva and vagina | 1 |
| | distinct, affecting the whole of the vulva and vagina | 2 |
| | severe, affecting the whole of the vulva and vagina | 3 |
| B. | Oedema | |
| | slight, confined to parts of the vulva and vagina | 1 |
| | distinct, affecting the whole of the vulva and vagina | 2 |
| | severe and extensive, affecting vulva-vagina and perineum | 3 |
| C. | Vesiculation, ulceration (vulvovaginal) | |
| | discrete vesicles in 1-2 quadrants | 1 |
| | confluent vesicles in 1-2 quadrants or vesicles in 3-4 quadrants, ulceration | 2 |
| | confluent vesicles in all quadrants, ulceration | 3 |
| | Maximum score (A-C) | 9 |

Ulcerations are observed mostly from the 14th day after infection onwards.

Assessment of Therapeutic Effect a) Number of animals showing regression of local symptoms by ≧66% between days 7 and 14, in comparison with those on day 3.

b) Number of animals showing complete regression between days 20 and 21.

c) Course of regression (mean score) between Days 3 and 21.

Differences between treated and untreated groups may be examined by means of the $X^2$-test (contingency tables), the significance level being $\alpha=0.01$.

A complete description of this model can be found in two publications by Lukás et al. [Archiv ges. Virusforsch. 44, 153–155 (1974) and Arch. Virol. 49, 1–11 (1975) Springer Verlag].

Procedure

The number indicated in the following Table of female albino guinea pigs of the Pirbright strain (150–180 g body weight) are infected intravaginally with ~$10^4$ PFU (plaque-forming units) of herpes simplex type 2 virus, cultivated in HEL (human embryonal lungs)

cells, as described in B. Lukás et al., Arch. ges. Virusforsch. 44, 153-155 (1974).

Beginning 72 h after infection, animals are treated intravaginally twice a day for 5 days with 0.2 ml of a gel containing one of the following: i) alpha interferon $B_1D_2B_3B_4$ at $1.5\times10^6$ units/kg; ii) Liposome-encapsulated MTP-PE at 1 mg/kg and iii) a mixture of both. Guinea pigs receiving placebo treatment are given a gel without active ingredients. This gel has the following composition:

| | |
|---|---|
| 2.25 % | sodium carboxymethylcellulose (Hercules, USA) |
| 10% | glycerine |
| made up to 100% | with bi-distilled water |

The symptoms occurring in untreated animals are described in B. Lukás et al., Arch. Virol. 49, 1-11 (1975).

B. Results

The following table summarizes the data from an experiment in which alpha interferon $B_1D_2B_3B_4$ is used either alone or in combination for the treatment of guinea pigs with herpes genitalis. As illustrated in experiments 1 and 2 the therapeutic effects (as determined by mean lesion scores) of alpha interferon $B_1D_2B_3B_4$ and MTP-PE are enhanced when both drugs are combined. The dosage of alpha interferon $B_1D_2B_3B_4$ used is equivalent to 10 μg/kg while the dosage of MTP-PE is 1000 μg/kg. This MTP-PE:interferon ratio of 100:1 is, therefore, comparable to that used in Example 2.

amount of a combination of components A and B wherein the individual components A and B are present in an amount each enhancing the antiviral activity of the other.

3. A preparation according to claim 1 wherein the ratio by weight of B versus A is 0.4/1 to 400/1.

4. A preparation according to claim 1 wherein the ratio by weight of B versus A is 1/1 to 100/1.

5. A preparation according to claim 1 wherein the pharmaceutically acceptable carrier comprises liposomes made from synthetical phosphatidylcholine and a pharmaceutically acceptable salt of a synthetical phosphatidylserine.

6. A method of treating warm-blooded animals suffering from a disease caused by viruses comprising administering to said animal an antivirally effective amount of the hybrid polypeptide $B_1D_2B_3B_4$ as component A and a pharmaceutically acceptable salt of N-acetyl-muramyl-L-alanyl-D-isoglutaminyl-L-alanine-2-(1,2-dipalmitoyl-sn-glycero-3-hydroxyphosphoryloxy)-ethylamide as component B in a weight ratio of B to A of 0.4/1 to 400/1.

7. A method according to claim 6 wherein said virus is Herpesviridae.

8. A method according to claim 7 wherein said virus is Herpes simplex viruses type 1 or 2.

9. A method according to claim 6 wherein the ratio by weight of B versus A is 1/1 to 100/1.

10. A method according to claim 6 wherein the ratio by weight of B versus A is 10/1 to 40/1.

11. A method according to claim 6 wherein the components A and B are administered in liposomes made Topical Effects of α-interferon $B_1D_2B_3B_4$ and MTP-PE Alone and in Combination in Guinea Pigs Infected Intravaginally with HSV-2/MS

| | Mean Lesion Score ± Standard Error | | | | | | |
|---|---|---|---|---|---|---|---|
| Days After Infection | 3 | 5 | 7 | 10 | 12 | 14 | 17 |
| Placebo | 2.2 ± 0.36 | 5.8 ± 1.16 | 6.5 ± 1.10 | 6.0 ± 1.13 | 3.8 ± 1.32 | 2.7 ± 1.20 | 3.7 ± 1.47 |
| Interferon $B_1D_2B_3B_4$ | 1.9 ± 0.18 | 4.1 ± 1.12 | 4.8 ± 1.36 | 4.7 ± 1.45 | 3.4 ± 1.44 | 2.9 ± 1.42 | 3.5 ± 1.43 |
| MTP-PE | 1.9 ± 0.23 | 2.8 ± 1.15 | 4.3 ± 1.32 | 4.0 ± 1.93 | 4.3 ± 1.42 | 4.3 ± 1.42 | 3.0 ± 1.60 |
| Interferon $B_1D_2B_3B_3$ + MTP-PE | 1.8 ± 0.20 | 1.3 ± 0.54 | 1.2 ± 0.66 | 0.9 ± 0.48 | 0.6 ± 0.40 | 0.6 ± 0.31 | 0.6 ± 0.27 |

We claim:

1. A pharmaceutical combination preparation for the treatment of an infection caused by viruses or for the activation of macrophages in a warm-blooded animal comprising an antivirally effective or macrophages activating amount of a combination of the hybrid α-interferon polypeptide $B_1D_2B_3B_4$ as component A and a pharmaceutically acceptable salt of N-acetyl-muramyl-L-alanyl-D-isoglutaminyl-L-alanine-2-(1,2-dipalmitoyl-sn-glycero-3-hydroxy phosphoryloxy)-ethylamide as component B together with a pharmaceutically acceptable carrier.

2. A preparation according to claim 1 for the treatment of an infection caused by viruses in a warm-blooded animal comprising an antivirally effective from synthetical phosphatidylcholine and a pharmaceutically acceptable salt of a synthetical phosphatidylserine.

12. A method of activating macrophages or of treating an infection caused by Herpesviridae in a warm-blooded animal comprising administering to said animal a macrophages activating or antivirally effective amount of a combination of the hybrid α-interferon polypeptide $B_1D_2B_3B_4$ as component A and a pharmaceutically acceptable salt of N-acetyl-muramyl-L-alanyl-D-isoglutaminyl-L-alanine-2-(1,2-dipalmitoyl-sn-glycero-3-hydroxyphosphoryloxy)-ethylamide as component B wherein the ratio by weight of B versus A is 1/1 to 100/1.

* * * * *

UNITED STATES PATENT AND TRADEMARK OFFICE
CERTIFICATE OF CORRECTION

PATENT NO. : 5,137,720

DATED : August 11, 1992

INVENTOR(S) : GANGEMI ET AL.

It is certified that error appears in the above-identified patent and that said Letters Patent is hereby corrected as shown below:

Column 16, line 31, change "claim 6" to --claim 9--.

Signed and Sealed this

Twenty-first Day of September, 1993

Attest:

BRUCE LEHMAN

*Attesting Officer*     *Commissioner of Patents and Trademarks*